US00PP24872P3

(12) United States Plant Patent
Olesen

(10) Patent No.: US PP24,872 P3
(45) Date of Patent: Sep. 16, 2014

(54) ROSE PLANT NAMED 'POULTY010'

(50) Latin Name: ***Rosa* hybrid**
Varietal Denomination: Poulty010

(75) Inventor: Mogens Nyegaard Olesen, Fredensborg (DK)

(73) Assignee: Poulsen Roser R/S, Fredensborg (DK)

( * ) Notice: Subject to any disclaimer, the term of this patent is extended or adjusted under 35 U.S.C. 154(b) by 217 days.

(21) Appl. No.: 13/507,008

(22) Filed: May 31, 2012

(65) Prior Publication Data

US 2013/0326749 P1 Dec. 5, 2013

(51) Int. Cl.
*A01H 5/00* (2006.01)

(52) U.S. Cl.
USPC ..... Plt./119

(58) Field of Classification Search
USPC ..... Plt./119
See application file for complete search history.

(56) References Cited

U.S. PATENT DOCUMENTS

PP14,390 P3 * 12/2003 Olesen et al. ..... Plt./119
PP16,148 P2 * 12/2005 Olesen et al. ..... Plt./122
PP21,509 P2 * 11/2010 Eskelund ..... Plt./119
PP23,324 P2 * 1/2013 Bedard ..... Plt./119

OTHER PUBLICATIONS

UPOV 201305 PLUTO QZ Data for 'Poulty010' Aug. 15, 2011.*
UPOV 201305 CA Data for 'Poulty010' Apr. 30, 2013.*

* cited by examiner

*Primary Examiner* — Wendy C Haas

(57) ABSTRACT

A new miniature rose plant that has abundant, orange red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty010'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2005 and the resulting seeds were planted in a controlled environment in Fredensborg, Denmark. The new variety, named 'Poulty010', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant orange red flowers;
2. Vigorous and compact growth;
3. Year-round flowering under heated and unheated glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty010' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty010' was selected by the inventor as a single plant from the progeny of the hybridization in 2005.

Asexual reproduction of 'Poulty010' by cuttings was first done by Mogens N. Olesen in the nursery in Fredensborg, Denmark in 2006. This initial and other subsequent propagations conducted in controlled environments have demonstrated that the characteristics of 'Poulty010' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty010'. Specifically illustrated in the drawing are flowers at various stages of development, flower in parts, leaves, and stems.

DETAILED DESCRIPTION OF THE VARIETY

The following is a description of 'Poulty010', as observed in its growth in glasshouses in Burlington, Ontario Canada. Observed plants are 2 months of age and were cultivated in 10.5 cm pots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148 are compared to 'Poulty010' in Chart 1.

CHART 1

| | 'Poulty010' | 'Poulpar029' |
|---|---|---|
| Petalage: | 35 | 30 |
| Flower Diameter: | 35 to 45 mm | 35 mm |
| General Tonality of Flower Color: | Orange-Red Group 33A | Red Group 53A |

FLOWER AND FLOWER BUD

Blooming habit: Continuous.

Flower bud:

*Size.*—Upon opening, 20 mm in length from base of receptacle to end of bud. 10 mm in diameter.

*Bud form.*—Ovate.

*Bud color.*—As sepals unfold, petals are Red Group 41A.

*Sepals.*—Upper Surface: Color: Green Group 138B. Texture: Smooth, strong pubescence. Lower Surface: Color: Yellow Green Group 144A. Texture: Smooth. Many fragrant stipitate glands. Shape: Apex: Cirrhose. Base: Flat at union with receptacle. Margins: Entire. No foliaceous appendages. Size: 20 mm long by 4 mm wide.

*Receptacle.*—Surface Texture: Smooth. Shape: Campanulate. Size: 5 mm tall and 4 mm wide. Color: Yellow Green Group 144A.

*Pedicel.*—Surface: Smooth. Length: 20 to 30 mm. Diameter: Generally 2 mm. Color: Yellow-Green Group 144A. Strength: Medium strength.

*Borne.*—1 to 3 flowers per stem.

Flower bloom:

*Fragrance.*—Light floral scent.

*Duration.*—As a pot plant, flowers last up to 28 days.

*Size.*—Flower diameter is 35 to 45 mm when open. Flower depth is 15 mm.

*Form.*—General shape is a hybrid tea with a high pointed center.

*Shape of flower, side view.*—The upper and lower portion is a flattened convex.

Petalage: Under normal conditions, flowers have 35 petals total, 5 of which are petaloids.

Color:

*General tonality.*—On open flower Orange Red Group 33A. No changes.

*Upon & after opening.*—Outermost and innermost petals are Orange-Red Group 33A with a petal spot of White Group 155B on the upper surface. Red Group 43C on the lower surface with a White Group 155B petal spot.

Petal characteristics:

*Petal reflex.*—Moderate.

*Margin.*—Entire, and uniform, moderate undulations.

*Shape.*—Generally narrow and elliptic. Apex shape: Rounded. Base shape: Acute.

*Size.*—18 mm (l) by 15 mm (w).

*Texture.*—Smooth.

*Thickness.*—Average.

Petaloids:

*Quantity.*—5 on average.

*Shape.*—Asymmetric. Rounded apex and acute base.

*Color.*—Orange-Red Group 33A on the upper surface. Red Group 43C on the lower surface. Petal spot at the base and vertical streaks Yellow Group 4D.

*Size.*—8 mm (l) by 4 mm (w).

Reproductive organs:

*Pollen.*—None Observed.

*Anthers.*—Size: 2 mm long. Color: Greyed-Orange Group 163B. Quantity: 30 on average.

*Filaments.*—Color: Greyed-Orange Group 163B. Length: About 2 to 3 mm.

*Pistils.*—Length: About 3 mm long. Quantity: 35 on average.

*Stigmas.*—Level relative to the length of the filaments and the height of the anthers. Color: Greyed-Yellow Group 162B.

*Styles.*—Color: Greyed-Red Group 180C.

*Seed formation.*—Not observed.

PLANT

Plant growth.—Upright, somewhat bushy. Plants are about 10 to 15 cm in height, and 10 to 15 cm wide.

Stems:

*Color.*—Juvenile growth: Yellow-Green Group 146A. Mature growth: Yellow-Green Group 146A.

*Length.*—Canes are about 6 cm from the base of the plant to the flowering portion.

*Diameter.*—3 to 4 mm.

*Internodes.*—On mature canes, there is an average distance of 12 mm between nodes.

*Surface texture.*—Young and mature wood is smooth.

Long prickles:

*Incidence.*—8 per 10 cm of stem.

*Size.*—Average length: 5 mm.

*Color.*—Juvenile prickles are Greyed-Orange Group 174B. Mature prickles are Greyed-Red Group 181A.

*Shape.*—Linear.

Plant foliage:

*Compound leaf size.*—70 mm (l) by 45 mm (w).

*Quantity.*—4 leaves per 10 cm of stem.

*Color of juvenile foliage.*—Upper Leaf Surface: Yellow-Green Group 144A. Lower Leaf Surface: Yellow-Green Group 144A. Margins: Greyed-Red Group 181A.

*Color of mature foliage.*—Upper Leaf Surface: Yellow-Green Group 147A. Lower Leaf Surface: Yellow-Green Group 147B.

Plant leaves and leaflets:

*Stipules.*—Size: About 4 mm in length. Shape: Linear, slightly broad based with outward extending species. Margins: Finely serrated with few stipitate glands. Color: Yellow-Green Group 144A.

*Petiole.*—Length: 12 mm on average. Diameter: About 2 mm. Upper surface: Yellow-Green Group 146B with intonations of Greyed-Purple Group 183B. Lower surface: Yellow-Green Group 144A. Small prickles.

*Rachis.*—Length: 30 mm on average. Diameter: About 1 to 2 mm. Upper surface: Yellow-Green Group 146B with intonations of Greyed-Purple Group 183B. Lower surface: Yellow-Green Group 144A. Small prickles.

*Leaflet.*—Number of leaflets: 5 on normal leaves in middle of the stem. Size: 30 mm in length by 15 mm wide. Margin: Serrate. General Shape: Ovate. Apex Shape: Aristate. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulty010', substantially as illustrated and described herein, due to its abundant, orange red flowers, vigorous growth, compact habit, suitability for production from softwood cuttings in pots, and durable flowers and foliage that make the variety suitable for distribution in the floral industry.

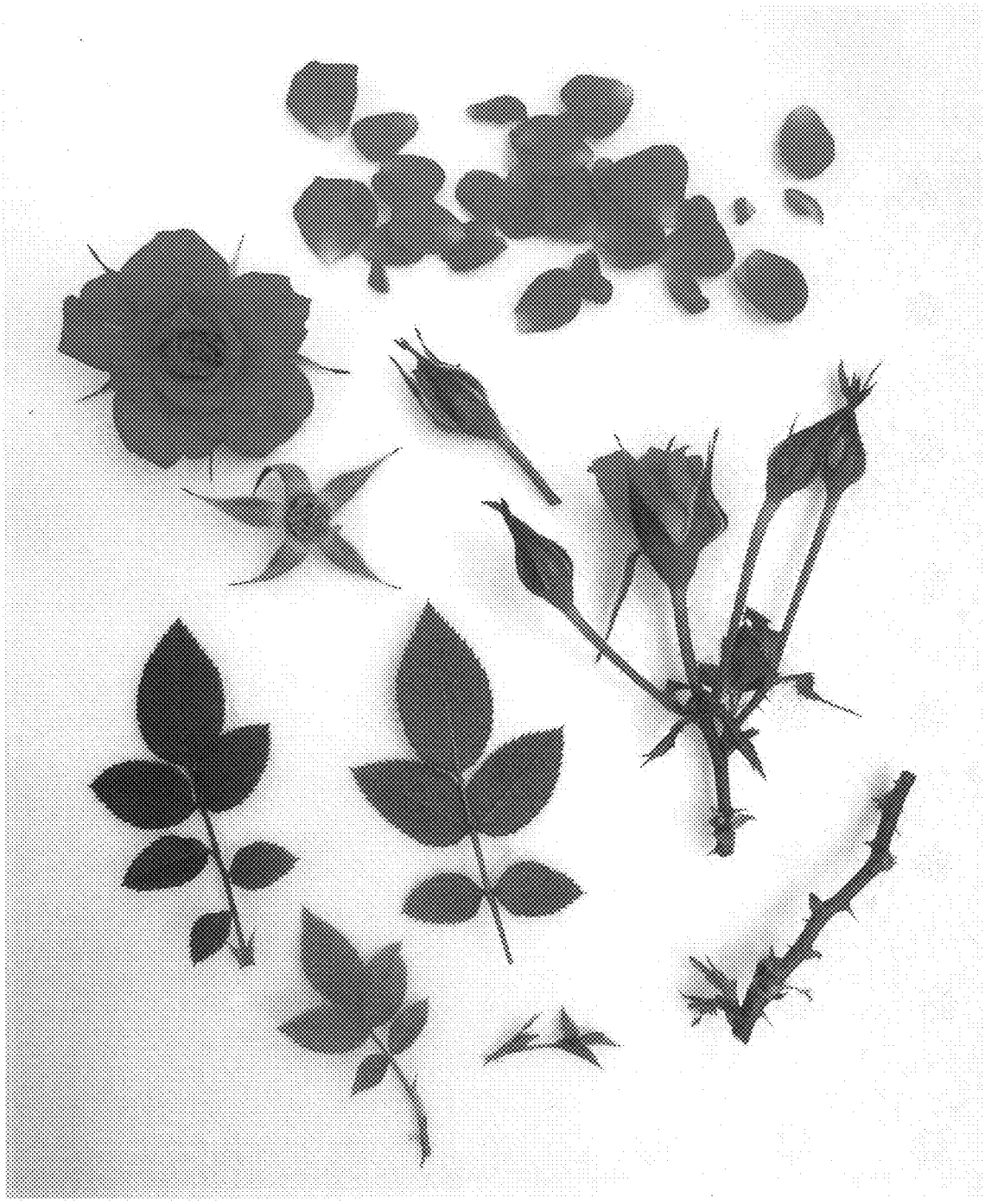

* * * * *